(12) United States Patent
Montgomery

(10) Patent No.: US 6,475,469 B1
(45) Date of Patent: Nov. 5, 2002

(54) COMPOSITIONS FOR REMOVING TOOTH STAINS

(75) Inventor: R. Eric Montgomery, Monterey, MA (US)

(73) Assignee: Applied Dental Sciences, Inc., Lee, MA (US)

(*) Notice: Subject to any disclaimer, the term of this patent is extended or adjusted under 35 U.S.C. 154(b) by 0 days.

(21) Appl. No.: 09/395,838

(22) Filed: Sep. 14, 1999

Related U.S. Application Data

(63) Continuation of application No. 08/974,740, filed on Nov. 19, 1997, now abandoned.
(60) Provisional application No. 60/031,339, filed on Nov. 21, 1996.

(51) Int. Cl.[7] .................................................. A61K 7/16
(52) U.S. Cl. ......................................... 424/49; 424/401
(58) Field of Search ..................... 424/49, 401

(56) References Cited

U.S. PATENT DOCUMENTS

| | | | | |
|---|---|---|---|---|
| 4,985,236 A | * | 1/1991 | Ibrahim et al. | ............... 424/52 |
| 5,178,869 A | * | 1/1993 | Ebine et al. | ................ 424/401 |
| 5,525,330 A | * | 6/1996 | Gaffar et al. | ................. 424/52 |

FOREIGN PATENT DOCUMENTS

| | | | |
|---|---|---|---|
| JP | 5-6523 | * | 5/1993 |
| WO | WO 97/45096 | * | 12/1997 |

* cited by examiner

*Primary Examiner*—Ralph Gitomer
(74) *Attorney, Agent, or Firm*—Banner & Witcoff, Ltd.

(57) ABSTRACT

An oral composition for removing tooth stains, such as those caused by an association of a chromogen with a layer of proteinaceous acquired pellicle on a tooth surface is provided. The composition includes (i) a destabilizing agent to disassociate and solubilize the chromogen from the layer of proteinaceous acquired pellicle, and (ii) a complexing agent having affinity for the disassociated chromogen to prevent its reassociation with the layer of proteinaceous acquired pellicle. The oral care composition is formulated to provide an oral pH equal to or above a pH for destabilizing the chromogen from its bond to the proteinaceous acquired pellicle, but less than a pH which can destabilize the chromogen from its bond to the complexing agent.

8 Claims, No Drawings

COMPOSITIONS FOR REMOVING TOOTH STAINS

RELATED U.S. APPLICATION(S)

This application is a continuation of U.S. application Ser. No. 08/974,740, filed Nov. 19, 1997 now abandoned that claims priority from U.S. provisional application Ser. No. 60/031,339, filed Nov. 21, 1996. Both of these related applications are hereby incorporated herein by reference.

TECHNICAL FIELD

The present invention relates to oral care compositions, and more particularly, to oral care compositions for removing tooth stains.

BACKGROUND ART

Within the past decade, there has been an increase in interests for oral care products which can effectively improve the appearance of teeth, and more particularly, in oral care products which can remove tooth stains and whiten teeth. In general, tooth staining results from accumulated interactions of tooth components, such as, enamel, dentin, proteinaceous acquired pellicle, plaque, and tartar with external chromogens (e.g., chromogen-containing foodstuffs, beverages, tobacco, etc.) and internal chromogens (e.g., tetracycline, blood, etc.). The ability of each of the above tooth components to absorb and retain the external and/or internal chromogens is dependent upon the chemical and physical nature of both the tooth component and the associated chromogen.

In response to the interests in oral care products which can effectively improve the appearance of teeth, oral care companies have offered a variety of approaches to improving the appearance of teeth, including dentist-supervised in-office procedures, such as the use of high concentrations of peroxide and/or lasers, dentist-supervised take-home products, such as peroxide-containing gels and pastes administered to the patient in a custom made dental tray, and a multitude of over-the-counter (OTC) gel, paste, rinse, and spray products. Currently, the safety and/or effectiveness of over-the-counter gels and pastes which contain peroxides (often formulated at an acidic pH to improve stability) or other oxidizing agents intended to whiten teeth is still being debated, regardless of the manner in which the gels or pastes are being administered, for instance, by way of a dental tray or toothbrushing.

The removal of tooth stains may also be accomplished by utilizing an abrasive dentifrice or prophylaxis paste or gel to scrape off, for instance, a film of proteinaceous acquired pellicle and its associated chromogens through toothbrushing and/or dental prophylaxis. In general, the higher the level of abrasivity of a composition, the greater the extent to which the stained acquired pellicle may be removed. Highly abrasive compositions, however, have been known to remove layers of mineralized tissue from tooth enamel and dentin, in addition to the layer of acquired pellicle. As a result, both consumers and dental practitioners have expressed concerns over the possibility of damage to the enamel and dentin from highly abrasive toothpastes and gels.

A number of oral care compositions have been developed to address the above concerns. These compositions, however, have not always provided satisfying results. Specifically, when using pastes or gels, in order to obtain a visible difference in tooth whitening, those compositions which contain a relatively low level of oxidizing agents and/or acidic pH, may still employ highly abrasive materials. As the use of highly abrasive materials can damage the tooth enamel, those compositions may not always be used on a daily basis. For those oral care compositions which contain a relatively low level of abrasive materials, and for those compositions which contain a relatively low level of oxidizing agents, as well as a low level of abrasive materials, the degree to which a visible difference in tooth whiteness is noticeable has been disappointing.

It would thus be desirable to provide an effective composition for removing tooth stains without the use of oxidizing agents and/or an unduly high amount of highly abrasive components, so that the composition may be used on a daily basis without concern for damage to the oral mucosa, tooth enamel or dentin.

SUMMARY OF THE INVENTION

The present invention, in a preferred embodiment, is directed to removing tooth stains caused by the binding of chromogenic substances (referred to below as "tannins" or "phenolic compounds")to the proteinaceous acquired pellicle on the tooth.

To remove such tooth stains, the present invention provides, in one embodiment, a novel oral care composition which includes (i) a destabilizing agent to disassociate and solubilize the chromogen from the layer of proteinaceous acquired pellicle, and (ii) a complexing agent having affinity for the disassociated chromogen to prevent its reassociation with the layer of proteinaceous acquired pellicle. The oral care composition of the present invention is preferably formulated to provide an oral pH equal to or above a pH for destabilizing the chromogen from its bond to the proteinaceous acquired pellicle, but less than a pH which can destabilize the chromogen from its bond to the complexing agent. In a preferred embodiment, the oral pH to be achieved by the composition is between approximately 7.0 and approximately 10.5. The composition may be in the form of a dentifrice, mouthrinse, chewing gum, or any other oral care delivery system providing sufficient oral contact time to permit destabilization of the bond between the chromogen and proteinaceous acquired pellicle and to allow for the complexing of the phenolic compound with the complexing agent.

In another embodiment, the present invention provides a process for manufacturing an oral care composition for removing tooth stains. The process includes first providing a water-soluble alkaline compound capable of disassociating a chromogen from a layer of proteinaceous acquired pellicle and obtaining a polymeric substance having affinity for the disassociated chromogen to prevent the chromogen from reassociating with the pellicle. A mixture of the polymeric substance and the alkaline compound is then created, so that when in use, an oral pH that is at least equal to a pH for destabilizing the chromogen from its bond to the proteinaceous pellicle, but less than a pH which can destabilize the chromogen from its bond to the polymeric substance. Once the mixture is created, the oral care composition is formulated from the mixture.

In a further embodiment of the invention, a method is provided for removing tooth stains. The method includes the steps of disassociating a chromogen from a layer of proteinaceous acquired pellicle on a tooth surface, and forming a complex between the disassociated chromogen and a polymeric substance having affinity for the chromogen to prevent reassociation of the chromogen with the proteinaceous acquired pellicle. In one embodiment of the method of the present invention, a composition may be provided which can disassociate the chromogen from the layer of acquired pellicle and which can form a complex between the chromogen and a polymeric substance.

DETAILED DESCRIPTION OF SPECIFIC EMBODIMENTS

The term "acquired pellicle" or "proteinaceous acquired pellicle" refers to a non-mineralized protein film, which tends to form when saliva contacts a clean tooth surface.

The term "tannin" refers to chromogenic substances and encompasses compounds known as phenolics which form tooth stains when complexed with the acquired pellicle on a surface of a tooth.

"Phenolic compound", as used hereinafter, refers to a compound having one or more benzene rings with at least one hydroxyl group attached directly to a benzene ring. Examples of phenolic compounds in foods and beverages include phenolic acids, coumarins, flavonoids, and polyphenolics.

Generally, after a tooth surface has been aggressively cleaned, such as that occurring during a dental prophylaxis with a pumice paste, the negatively-charged enamel surface on the tooth is exposed and is almost immediately contacted by saliva. Saliva contains components such as calcium ions and proline-rich proteins (PRP), which readily interact with amino acid side chains on the newly exposed negatively-charged enamel surface to form a proteinaceous film. This proteinaceous film tends to resist solubilization, even in highly acidic media, and may not dislodge, even by the constant salivary flow through the oral cavity. The strong interactions between the calcium ions and the amino acid side chains of the proteinaceous film, in addition to interaction with the inorganic hydroxyapatite component of enamel on the tooth surface may contribute to the film's resistance to solubilization. Further accumulation of organic material from saliva, bacteria, gingival crevicular fluid, blood and other exogenous materials including food, dental materials, and oral hygiene products on the film can lead to the formation of the acquired pellicle.

Once formed, the proteinaceous acquired pellicle acts as a point of attachment for plaque-forming bacteria, which can lead to the development of a mature plaque matrix and, upon mineralization, to tartar. In addition, the proteinaceous acquired pellicle is highly interactive with dietary substances collectively known as tannins. Tannins, as indicated above, includes phenolic compounds, which when interact with proteins, such as the proteinaceous acquired pellicle, forms substantially insoluble complexes. (This complex will be hereinafter referred to as a "tannin-protein complex"). The formation or precipitation of the tannin-protein complex can subsequently lead to the formation of tooth stains. These tooth stains can be particularly difficult to remove because of the strength of the interaction between the tannin and the proteinaceous acquired pellicle. It should noted that the interaction of tannins, including phenolic compounds, with proteins to form insoluble complexes is well known and well described in the art.

To remove or enhance the removal of tooth stains, the present invention provides, in a preferred embodiment, an alkaline destabilizing agent to disassociate chromogenic tannin from the proteinaceous acquired pellicle, and a polymeric complexing agent having affinity for the disassociated chromogenic tannin to prevent reassociation of such chromogenic tannin with the proteinaceous acquired pellicle.

In one embodiment of the invention, the destabilizing agent may be a water-soluble alkaline compound. The alkaline compound preferably has a relatively low level of toxicity, so that it may be safely used to formulate an oral care composition. The preferred alkaline compound may be selected from the group consisting of alkali metals of an inorganic anion, ammonium salts of an inorganic anion, alkaline metals of an organic anion, ammonium salts of an organic anion, and combinations thereof. Examples of an inorganic anion are phosphate, polyphosphate, hydroxide, carbonate, bicarbonate, and borate. Examples of an organic anion are acetate, citrate, and lactate.

The complexing agent, on the other hand, may be a polymer that is capable of strongly interacting with the phenolic moieties of tannin, so that an insoluble complex between tannin and the complexing agent is formed. Particularly, the complexing agent of the present invention preferably has a higher affinity for the soluble tannin disassociated from the proteinaceous acquired pellicle, so that such tannin does not reassociate itself with the proteinaceous acquired pellicle.

In a preferred embodiment, polymers and copolymers (hereinafter referred to collectively as "(co)polymers")of vinyl pyrrolidone, such as poly (vinyl pyrrolidone) and poly (vinyl pyrrolidone-co-vinyl acetate) are useful as a complexing agent. These (co)polymers have a molecular weight ranging up to about 60,000 Daltons, as determined by high-performance gel permeation chromatography, are water soluble, and tend to have a low toxicity level. As such, they are suitable for inclusion in the formation of the oral care composition of the present invention. Molecular weight may also be expressed in terms of an intrinsic viscosity, or K-value. The (co)polymers of vinyl pyrrolidone may, therefore, have a K-value ranging up to about 30. K-values are typically included in commercial specification of a particular (co)polymer, for instance, Kollidon 25 (k-value 25), a material manufactured by BASF Corporation. It should be appreciated that the vinyl pyrrolidone (co) polymers of the present invention, when included in an oral care composition at a concentration sufficiently high to effectively complex with a polyphenolic compound (i.e., tannin) disassociated from the proteinaceous acquired pellicle, do not appreciably contribute to the viscosity of the oral care composition.

(Co)polymers of ethylene oxide, such as polyethylene glycol, may also be used as a complexing agent for tannin which has disassociated from the acquired pellicle. In a preferred embodiment, polyethylene glycol has a molecular weight between about 2,000 Daltons and about 10,000 Daltons. At this molecular weight, similar to the (co) polymers of vinyl pyrrolidone, polyethylene glycol does not contribute significantly to the viscosity of the oral care composition. Polyethylene glycol is also low in oral toxicity, and is therefore suitable for use as a complexing agent in the oral care composition of the present invention.

The polymers and copolymers disclosed above are suitable as complexing agents because it is believed that each forms a complex with a solubilized tannin or polyphenolic substance disassociated from the proteinaceous acquired much more readily than the recomplexing of the such tannin or polyphenolic substance to the acquired pellicle. Although not wishing to be bound by any one particular theory, it is believed that the complexing polymers and copolymers, with a relatively high affinity for disassociated and solubilized tannin when compared to the acquired pellicle, act as anti-redeposition agents by scavenging and binding the such tannin, thereby preventing recomplexing of the tannin with the proteinaceous acquired pellicle.

In order to maintain a high affinity for the solubilized tannin disassociated from the acquired pellicle, the oral care composition of the present invention is formulated so that during use, a specific oral pH is achieved. Such pH is preferably substantially equal to or above a pH for destabilizing the tannin-protein complex, so that tannin may disassociate from the proteinaceous acquired pellicle, but less than a pH for destabilizing the complex between the tannin and a complexing agent. It has been found that an oral care composition formulated to achieve an oral pH of at least 7.0 is capable of providing the desired effect. An oral pH in a range of from between 7.0 and 10.5 is preferred.

The composition, of course, may contain other components typically found in oral care compositions, including flavoring agents and detergents/surfactants, examples of which include but are not limited to, sodium lauryl sulfate and sodium methyl cocoyl taurate. When a surfactant is used the concentration should be limited to that suitable for use within the cavity. A concentration of less than 5% by weight is preferred.

The delivery system for use with the composition of the present invention preferably includes any oral care delivery system with a sufficient contact time in the oral cavity to destabilize the staining tannin-protein complex. Examples of preferred delivery systems include toothpastes, mouthwashes, chewing gums, treatment gels, and others systems having utility in the application of the present composition. It should be noted, that immediately upon destabilizing the staining tannin-protein complex, the complexing polymer or copolymer will bind the soluble tannin, thus preventing it from recomplexing with proteinaceous acquired pellicle and restaining the tooth.

The following examples serve to illustrate a number of oral care compositions, in the form of toothpastes, which are useful in practicing the embodiments of the present invention. The examples, however, are not intended to limit the scope of the present invention.

EXAMPLE I

Table 1 below shows five different dentifrice (i.e., oral care) compositions. Dentifrice compositions B–E include a preferred alkaline destabilizing agent, namely, sodium tripolyphosphate, and a complexing agent, either poly(vinyl pyrrolidone) or polyethylene glycol, which together effectively remove tooth stains without being unduly abrasive to tooth enamel and dentin. Dentifrice composition A, on the other hand, is a placebo, having neither a destabilizing agent nor a complexing agent. It should be noted that the percentages to which Table 1 refers are by weight based on the total weight of the toothpaste.

TABLE 1

Components of 5 dentifrice compositions

| Ingredient | A % w/w | B % w/w | C % w/w | D % w/w | E % w/w |
| --- | --- | --- | --- | --- | --- |
| Sorbitol noncrystallizing solution | 42.000 | 37.000 | 15.800 | 19.293 | 12.660 |
| Deionized water | 20.510 | 20.510 | 20.260 | 26.817 | 29.650 |
| Sodium benzoate | 0.300 | 0.300 | 0.500 | 0.500 | 0.500 |
| Sodium saccharin | 0.300 | 0.300 | — | 0.400 | 0.550 |
| Sodium fluoride | 0.240 | 0.240 | 0.240 | 0.240 | 0.240 |
| Glycerin 99.7% | 8.000 | 8.000 | 7.000 | 18.000 | 18.000 |
| Xanthan Gum | 1.200 | 1.200 | 1.000 | — | — |
| Cellulose gum (CMC7MXF) | — | — | — | 0.900 | 1.000 |
| Titanium dioxide | 1.200 | 1.200 | — | 1.200 | 1.200 |
| Dicalcium phosphate dihydrate | — | — | 50.000 | — | — |
| Hydrated silica (Sylodent 7560) | 17.000 | 17.000 | — | 17.500 | 17.500 |
| Sodium Tripolyphosphate | — | 3.000 | 2.000 | 3.000 | 3.000 |
| Poly(vinyl pyrrolidone)K-30 | — | — | 1.000 | — | — |
| Poly(vinyl pyrrolidone)K-25 | — | 2.000 | — | 2.000 | — |
| Polyethylene glycol 6000 | — | — | — | — | 5.000 |
| Sodium lauryl sulfate | — | — | 1.200 | 0.600 | 0.600 |
| Sodium methyl cocoyl taurate | 0.800 | 0.800 | — | 0.600 | 0.600 |
| Sodium hydroxide (10% solution) | to pH 8.0 | to pH 8.0 | to pH 8.0 | to pH 7.5 | to pH 8.5 |
| Flavor | 0.450 | 0.450 | 1.000 | 0.450 | 1.000 |
| TOTAL | 100.00 | 100.000 | 100.000 | 100.000 | 100.000 |

Each of the dentifrice compositions listed in Table 1 may be prepared in the following manner. Sorbitol and deionized water were placed in a stainless steel container along with at least one of sodium benzoate, sodium saccharin and sodium fluoride, and mixed with a propeller-type mixer until a clear solution was obtained. Under constant agitation, titanium dioxide (if any), sodium tripolyphosphate (if any), and poly(vinyl pyrrolidone) or polyethylene glycol (if any) were added and dissolved. The resulting mixture constitutes Part A.

In a separate container, a slurry of glycerin and either xanthan or cellulose gum was mixed until a smooth suspension was achieved. The resulting mixture constitutes Part B.

Part B was then slowly added to Part A under constant stirring until a viscous solution was obtained. The viscous solution was next transferred to a vacuum double planetary mixer (Charles Ross & Sons, Haupauge, N.Y.), combined with either dicalcium phosphate or hydrated silicas, and mixed at high speed under 28" Hg vacuum until a smooth paste was obtained. Detergents (e.g., sodium lauryl sulfate and/or sodium methyl cocoyl taurate) were added and mixed at medium speed under 28" Hg vacuum until dissolved. The pH of this mixture was then determined and an adjustment was made with sodium hydroxide, if necessary, to provide a composition mixture with an overall pH of between about 7.5 and about 8.5, depending on the dentifrice composition being made. The composition mixture, when combined with distilled water at a ratio of 1 part dentifrice:3 parts distilled water, preferably provides a pH between about 7.0 and 10.5, similar to the desired oral pH when the composition is being used in the oral cavity. Following the pH adjustment, flavor was added and the entire mixture was blended to homogeneity at medium speed and 28" Hg vacuum. The finished dentifrice was packaged in foil/plastic laminated tubes with caps, and stored at room temperature until use.

EXAMPLE II

In accordance with an embodiment of the present invention, dentifrice composition B, from Table 1, and placebo dentifrice composition A were compared to determine the effectiveness of each in removing tooth stains. Composition B contains the destabilizing agent sodium tripolyphosphate, and the complexing agent poly(vinyl pyrrolidone), while composition A does not contain either of the destabilizing or complexing agents. Compositions A and B have substantially the same relatively low level of abrasivity.

The effectiveness of the novel dentifrice was determined as described below using a modified method of Stookey, G. K., et al, Journal of Dental Research 61(11):1236–1239, 1982.

Squares of dental enamel 4 mm on a side were cut, using a diamond cutting disk, from bovine permanent incisors. Using a mold, the enamel squares were embedded in clear polyester casting resin (NATCOL Crafts, Inc., Redlands, Calif.) to provide 1.5 cm square blocks with the labial surface exposed. The top surface of the polyester blocks was ground flush with the leveled labial surface of the enamel squares by means of a dental model trimmer. The surface was then smoothed by hand sanding on 400 grit emery paper using water as a lubricant until all grinding marks were removed. Finally, the top surface of the blocks was hand polished to a mirror finish using a water slurry of GK1072 calcined kaolin (median particle size=1.2 microns) on a cotton cloth. The finished specimens were examined under a dissecting microscope and were discarded if they had surface imperfections.

In preparation for the formation of artificial stained pellicle on the enamel, the specimens were etched for 60 seconds in 0.2M HCl followed by a 30-second immersion in a saturated solution of sodium carbonate. A final etch was performed with 1% phytic acid for 60 seconds, then the specimens were rinsed with deionized water and attached to the staining apparatus.

The pellicle-staining apparatus was constructed to provide alternate immersion into the staining broth and air-drying of the specimens. The apparatus included an aluminum platform base which supported a Teflon rod (¾ inch in diameter) connected to an electric motor. The motor, by means of a speed reduction box, rotated the rod at a constant rate of 1.5 rpm. Threaded screw holes were spaced at regular intervals along the length of the rod. The tooth specimens were attached to the rod by first glueing the head of a plastic screw to the back of a specimen. Thereafter, the plastic screw is tightened into a threaded screw hole in the rod. Beneath the rod was a removable, 300-ml capacity trough, which held a pellicle-staining broth.

The pellicle-staining broth was prepared by adding 1.02 grams of instant coffee, 1.02 grams of instant tea, and 0.75 grams of gastric mucin (Nutritional Biochemicals Corp., Cleveland, Ohio 44128) to 250 ml of sterilized trypticase soy broth. Approximately 50 ml of a 24-hour Micrococcus luteus culture was also added to the stain broth. The pellicle-staining apparatus, with the enamel specimens attached, and the staining broth in the trough was then placed in an incubator at 37° C. with the specimens rotating continuously through the staining broth and air. The staining broth was replaced once very 24 hours for ten consecutive days. With each broth change the trough and specimens were rinsed and brushed with deionized water to remove any loose deposits. On the eleventh day the staining broth was modified by the addition of 0.03 grams of $FeCl_3.6H_2O$. The modification of the broth was continued with daily broth changes until the stained pellicle film on the specimens was sufficiently dark. Once sufficiently dark, the specimens were removed from the staining broth, brushed thoroughly with deionized water, and refrigerated in a humidor until used.

The intensity of the extrinsic stained pellicle on the teeth was measured, as a "pre-test" reading, by taking diffuse reflectance absorbance readings with a Minolta C5031 spectrophotometer having a 3 mm aperture (Minolta Camera Co., Ramsey, N.J.). Absorbance measurements over the entire visible spectrum were obtained using the CIELAB color scale (Commission International de L'Eclairage, Recommendations on uniform color spaces, color difference equations, and psychometric color terms, Supplement 2 to CIE publication 15 (E-13.1) 1971 (TC-1.3), 1978, Paris: Beaurea Central de la CIE, 1978). The CIELAB color scale evaluates color in terms of three axes of a color sphere, called L, a, and b. The "L" value is the axis in the color sphere which relates lightness and darkness on a scale from 0 (black) to 100 (white). The "a" value is the axis which relates color on a yellow to blue scale, with a 0 value in the center of the sphere, positive values toward the yellow, and negative values toward the blue. The "b" value is the axis which relates color on a red to green scale, with a 0 value in the center of the sphere, positive values toward the red, and negative values toward the green.

The stained enamel specimens were allowed to air-dry at room temperature for at least one hour before absorbance measurements were made. Measurements were conducted by aligning the center of a 4-mm square segment of stained enamel directly over the 3-mm aperture of the Minolta spectrophotometer. An average of 3 absorbance readings using the L*a*b* factors were taken for each specimen.

In preparation for treatment, the specimens were stratified into equal groups of 16 specimens each, with each group having equivalent average baseline L*a*b* factor stain scores. The specimens were positioned on a V-8 mechanical cross-brushing machine (Manly, R. S.: The abrasion of cementum and dentin by modern dentifrices, Journal of Dental Research 20:583, 1941) equipped with soft, nylon-bristle toothbrushes (Ancodent No. 41, Anchor Brush Co., Aurora, Ill. 60507) and adjusted to have about 150 grams of pressure on the enamel surfaces.

The dentifrices A and B were tested as slurries consisting of 25 grams of dentifrice mixed with 50 grams of deionized water, and the specimens were brushed for 800 double strokes. To minimize mechanical variables, enamel specimens for each group were brushed during each run, and the test products were randomly assigned to each brush station until all products had been tested at all stations twice. Also, close attention was paid to alignment of enamel specimens in all planes to ensure uniformity of brushing patterns. Following brushing, the specimens were rinsed, allowed to dry for an hour, and absorbance readings made. Next, the specimens were pumiced using a dental handpiece in order to clean all residual stain off of the teeth. A "post-test" reflectance reading for each of the specimens was recorded. This technique provided a value for each specimen that represented the maximum amount of stained pellicle that potentially could be removed by a test dentifrice.

The difference between the pre-test and post-test readings for each color factor (L*, a*, and b*) represented the ability of the test dentifrice to clean extrinsic stained pellicle from teeth. The data were calculated and defined as follows:

(1) Stained Pellicle Removed=Baseline stain reading minus the reading after treatment.

(2) Total Stained Pellicle Available=Stain reading minus the reading following treatment and pumicing.

(3) % Total Stained Pellicle Removed="Stained Pellicle Removed" divided by the "Total Stained Pellicle Available".

The overall change in stained pellicle was calculated using the CIELAB equation $$\Delta E=[(\Delta L^*)^2+(\Delta a^*)^2+(\Delta b^*)^2]^{1/2}$$

The individual components of the L*a*b* factors were also analyzed separately to determine the specific changes in lightness, redness, and yellowness, respectively.

Statistical significance of data for each category was determined by analysis of variance, and intergroup comparisons were made by means of the Studentized Newman-Keuls (SNK) range test. Data were tabulated using a PC and spreadsheet program (Lotus 1-2-3, Version 2.01, 1986, Lotus Development Corp., Cambridge, Mass.). Summary print files were then loaded into a VAX 8530 mainframe computer and analyzed by means of a conventional statistics program (SAS, SAS Institute Inc., Cary, N.C.). All SNK comparisons were made using a 2-tail test.

TABLE 2

Effectiveness of the inventive dentifrice versus a placebo dentifrice

| Dentifrice | $\Delta E$ | % Reduction of Stain |
|---|---|---|
| A | 12.43 +/− 2.52 | 48% |
| B | 16.23 +/− 3.26 | 66% |

The study demonstrated an improvement in stain removal gained from the inclusion of the destabilizing agent sodium tripolyphosphate and the complexing agent poly(vinyl pyrrolidone) in dentifrice B, when compared against to the same dentifrice A without the destabilizing and complexing agents.

EXAMPLE III

Tooth stain removal studies were also conducted to determine the ability of some of the dentifrice compositions of the present invention, and in particular, dentifrice composition B, in removing tooth stains versus some non-peroxide, commercially available tooth whitening dentifrice compositions.

The procedure of Example II was repeated with each of commercial dentifrice compositions A, B, and C. Commercial dentifrices A (CD-A) and B (CD-B) claim to have a high level of stain removing capability due to the inclusion of greater than 4% w/w sodium tripolyphosphate in the formulations. Commercial dentifrice C (CD-C) is a popular whitening dentifrice having citric acid, hydrated alumina, and papain (a proteolytic enzyme) as the stain-removing components. The abrasivity of the commercial dentifrices versus that of the dentifrice B is as follows:

CD-A=CD-B=Inventive Dentifrice B>CD-C

TABLE 3

Effectiveness of inventive dentifrice versus commercial dentifrices

| Dentifrice | $\Delta E$ | % Reduction of Stain |
|---|---|---|
| Inventive Dentifrice B | 16.23 +/− 3.26 | 66% |
| Commercial Dentifrice A | 14.59 +/− 3.78 | 54% |
| Commercial Dentifrice B | 10.66 +/− 2.50 | 45% |
| Commercial Dentifrice C | 7.49 +/− 1.71 | 31% |

Dentifrice B, formulated in accordance with an embodiment of the present invention, performed very well when compared to commercial dentifrice compositions utilizing a variety of different technologies for removing or eliminating tooth stains. Dentifrice B, despite having a lower level of destabilizing agent, sodium tripolyphosphate (e.g., 3 percent by weight) (see Table 1) than commercial dentifrices CD-A and CD-B (e.g., more than 4 percent by weight), performed substantially better in reducing tooth stains. In addition, dentifrice B reduces tooth significantly better than commercial dentifrice CD-C.

What is claimed is:

1. A dentifrice for removing tooth stain caused by an association of a chromogen with a layer of proteinaceous acquired pellicle on a tooth within an oral cavity, the dentifrice comprising:
   about 2% to about 3% sodium tripolyphosphate by weight, to disassociate the chromogen from the layer of proteinaceous acquired pellicle; and
   about 1% to about 2% polyvinyl pyrrolidone, having affinity to the disassociated chromogen to prevent reassociation of the chromogen with the layer of proteinaceous acquired pellicle.

2. A dentifrice according to claim 1 further including a detergent, wherein the detergent is selected from the group consisting of sodium lauryl sulfate, sodium methyl cocoyl taurate, and combinations thereof, the detergent having a concentration from about 0.6% to less that 5% by weight.

3. A dentifrice according to claim 1 further providing an oral pH level that is between approximately 7.0 and approximately 10.5.

4. A dentifrice according to claim 1 further being provided in a carrier which provides sufficient oral contact time to permit disassociation of the chromogen from the layer of proteinaceous acquired pellicle and to allow association of the chromogen with the polyvinyl pyrrolidone.

5. A dentifrice for removing tooth stain caused by an association of a chromogenic phenolic compound with a layer of proteinaceous acquired pellicle on a tooth within an oral cavity, the dentifrice comprising:
   about 2% to about 3% w/w of sodium tripolyphosphate; and
   about 1% to about 2% polyvinylpyrrolidone;
   wherein the dentifrice provides an oral pH level between approximately 7.0 and approximately 10.5.

6. A dentifrice according to claim 5, the polyvinyl pyrrolidone having a K-value, the K-value being from about 25 to no greater than about 30.

7. A dentifrice according to claim 5, further including a detergent, wherein the detergent is selected from the group consisting of sodium lauryl sulfate, sodium methyl cocoyl taurate, and combinations thereof, the detergent having a concentration of from about 0.6% to less than 5% by weight.

8. A dentifrice according to claim 5 further being provided in a carrier which provides sufficient oral contact time to permit disassociation of the chromogen from the layer of proteinaceous acquired pellicle and to allow association of the chromogen with the polyvinyl pyrrolidone.

\* \* \* \* \*